United States Patent [19]

Schwan

[11] 4,052,400

[45] Oct. 4, 1977

[54] HYPERTENSIVE 1-SUBSTITUTED 2(1H)-PYRIMIDONES

[75] Inventor: Thomas J. Schwan, Norwich, N.Y.

[73] Assignee: Morton-Norwich Products, Inc., Norwich, N.Y.

[21] Appl. No.: 736,836

[22] Filed: Oct. 29, 1976

[51] Int. Cl.$^2$ .................. C07D 401/06; C07D 239/22
[52] U.S. Cl. .............................................. 260/256.4 C
[58] Field of Search .................................. 260/256.4 C

[56] References Cited

U.S. PATENT DOCUMENTS

| 3,681,349 | 8/1972 | Schwan et al. | 260/256.4 C |
| 3,941,789 | 3/1976 | Renth et al. | 260/256.4 C |

Primary Examiner—Donald G. Daus
Assistant Examiner—James H. Turnipseed
Attorney, Agent, or Firm—Anthony J. Franze

[57] ABSTRACT

1-Substituted-2(1H)-pyrimidones of the formula:

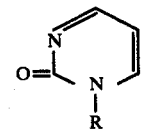

where R is 2-(N-piperidino)ethyl and 1-dimethylaminoisopropyl possess pharmacological activity as hypertensive agents.

3 Claims, No Drawings

HYPERTENSIVE 1-SUBSTITUTED 2(1H)-PYRIMIDONES

This invention relates to novel chemical compounds of the formula:

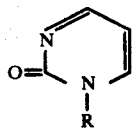

where R is 2-(N-piperidino)ethyl and 1-dimethylaminoisopropyl. When administered intravenously or intraperitonally to animals these compounds exhibit hypertensive activity. Administration of 50 and 100 mg/kg of these compounds to anesthetized dogs resulted in increases in mean arterial blood pressure for duratives of up to 95 minutes.

In order that this invention be readily available to and understood by those skilled in the art the following illustrative examples are supplied.

EXAMPLE I

1-[2-(N-piperidino)ethyl]-2-(1H)-pyrimidone dihydrochloride hemihydrate

2-Hydroxypyrimidine hydrochloride (39.9 g, 0.3 mole) in 700 ml of methanol was treated with sodium carbonate (95 g, 0.9 mole) followed by a solution of N-(2-chloroethyl)piperidine hydrochloride (55.2 g, 0.3 mole) and sodium iodide (23 g, 0.15 mole) in 200 ml methanol. The suspension was refluxed for 24 hrs, filtered, and the filtrate was concentrated to dryness in vacuo. The oil was dissolved in 250 ml of water and the solution was extracted with 3 × 750 ml of ether to give 38 g (61%) of the free base.

The hydrochloride was prepared by treating a methanol solution of the free base with methanolic hydrogen chloride.

An analytical sample, m.p. dec. 197°, was recrystallized from ethanol.

Anal. Calcd. for $C_{11}H_{17}N_3O.2HCl.1/2\ H_2O$: C, 45.68; H, 6.91; N, 14.53. Found: C, 45.93; H, 6.73; N, 14.31.

EXAMPLE II 1-(1-Dimethylaminoisopropyl)-2-(1H)-pyrimidone dihydrochloride

2-Hydroxypyrimidine hydrochloride (53.2 g, 0.4 mole) in 700 ml of methanol was treated with sodium carbonate (127.2 g, 1.2 moles) followed by 10 g of sodium iodide and 1- dimethylaminoisopropyl chloride hydrochloride (63.2 g, 0.4 mole) in 250 ml of methanol. The suspension was refluxed 24 hrs and concentrated to dryness in vacuo leaving a residue which was dissolved in 500 ml of water. The aqueous solution was treated with 20% sodium hydroxide to pH 11. Over a period of 48 hrs of continuous extraction with ether there was recovered 35 gms of free base (49%). The dihydrochloride was prepared by dissolving the free base in methanol, treating with methanolic hydrogen chloride, and removing the solvent in vacuo.

An analytical sample m.p. 210° dec. was recrystallized from ethanol.

Anal. Calcd. for $C_9H_{15}N_3O.2HCl$: C, 42.53; H, 6.74; N, 16.54 Found: C, 42.57; H, 6.82; N, 16.59

What is claimed is:

1. A compound of the formula:

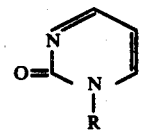

Where R is 2-(N-piperidino)ethyl and 1-dimethylaminoisopropyl.

2. The compound 1-[2-(N-piperidino)ethyl]-2(1H)-pyrimidone dihydrochloride hemihydrate.

3. The compound 1-(1-dimethylaminoisopropyl)-2(1H)-pyrimidone dihydrochloride.